US012788904B1

(12) United States Patent
Schafer

(10) Patent No.: US 12,788,904 B1
(45) Date of Patent: Nov. 10, 2026

(54) POWER JET NEBULIZER

(71) Applicant: Steven Charles Schafer, Erie, CO (US)

(72) Inventor: Steven Charles Schafer, Erie, CO (US)

( * ) Notice: Subject to any disclaimer, the term of this patent is extended or adjusted under 35 U.S.C. 154(b) by 0 days.

(21) Appl. No.: 19/436,414

(22) Filed: Dec. 30, 2025

(51) Int. Cl.
*A61M 11/02* (2006.01)

(52) U.S. Cl.
CPC .................................... *A61M 11/02* (2013.01)

(58) Field of Classification Search
CPC .... A61M 11/002; A61M 11/02; A61M 11/06; A61M 11/08; A61M 2206/00; B05B 7/00
See application file for complete search history.

(56) References Cited

U.S. PATENT DOCUMENTS 3,561,444 A 2/1971 Boucher
4,113,809 A 9/1978 Abair et al.
7,581,718 B1 * 9/2009 Chang .................. B05B 7/0012 261/78.2
8,042,536 B1 10/2011 Howey
12,102,751 B2 10/2024 Greenfield
2002/0112720 A1 * 8/2002 Abate .................. A61M 11/06 128/200.24
2012/0266872 A1 * 10/2012 Tanaka .................. A61M 11/06 128/200.21
2012/0318260 A1 12/2012 Hsieh et al.
2014/0190482 A1 7/2014 Wade
2014/0291414 A1 10/2014 Bretillot et al.
2016/0206835 A1 7/2016 Lee et al.
2016/0361506 A1 12/2016 Lin et al.
2019/0247599 A1 8/2019 Lee et al.
2020/0353187 A1 11/2020 Pell et al.
2023/0201487 A1 6/2023 Surber et al.

FOREIGN PATENT DOCUMENTS

CN 109172965 A * 1/2019 ............ A61M 11/02
EP 2952219 A1 * 12/2015 ............ A61M 11/06

OTHER PUBLICATIONS

English translation of CN-109172965-A (Year: 2019).*

* cited by examiner

*Primary Examiner* — Kendra D Carter
*Assistant Examiner* — Maap Ellabib
(74) *Attorney, Agent, or Firm* — Goldstein Law Offices, P.C.

(57) ABSTRACT

A power jet nebulizer configured to mix air with liquid medication and form a medicated wet vapor, comprising a bottom bowl with a base and a stem, an inverted funnel, a turbo cap, and a top bowl with an inlet port and an outlet port. The bottom bowl houses the inverted funnel, the turbo cap attaches to the bottom bowl, the top bowl attaches to the bottom bowl. Medication is inserted into the inlet port and translates downward, towards the base. The tubing of an air tank is attached to the stem, the air translates through the stem into the bottom bowl. The air mixes with the medication and includes a high pressure and high velocity which breaks down the medication, thereby converting the medication into vapor. The vapor translate upward into the top bowl, through the outlet port, and into a mask. The user then inhales the vapor.

23 Claims, 8 Drawing Sheets

POWER JET NEBULIZER

TECHNICAL FIELD

The present disclosure relates generally to a power jet nebulizer. More particularly, the present disclosure relates to a power jet nebulizer configured to provide wet vapor, thereby enabling easy, quick, and comfortable treatment.

BACKGROUND

Medical professionals have long recognized the importance of nebulizer treatments. Nebulizer treatments operate by turning medication into a mist which can be inhaled to address lung diseases or respiratory conditions, for example, chronic obstructive pulmonary disease, cystic fibrosis, and asthma. Patient's utilize a nebulizer for treatment for a range of time, some patients require use for a few days and other patients require lifetime use. For this reason, it is crucial for nebulizers to be easy, quick, and comfortable to use. However, traditional nebulizers do not address these concerns. Indeed, traditional nebulizers may be detrimental as they are time consuming, inefficient, and uncomfortable.

Currently, traditional nebulizers fail to address the need of easy, quick, and comfortable use. These nebulizers often dispense dry vapor which irritate the patient's airway and takes a longer time to penetrate the lungs. These nebulizers also frequently include limited air pressure, thereby resulting in the treatment taking a longer duration. Additionally, these traditional nebulizers often include a poor air filter which frequently gets clogged, may not be replaceable, and is restrictive thereby resulting in poor quality air being mixed with the medication. Traditional nebulizers also often operate by being plugged into an outlet, thereby limiting where patients can complete their treatment. Moreover, traditional nebulizer masks frequently are uncomfortable, easily dislodge from the tubing connected to the nebulizer, and include holes. These holes are often positioned on the sides of the mask, thereby resulting in a large quantity of vapor escaping and dispersing into the patient's face and hair. This causes the treatment to take longer and may irritate the patient. While traditional nebulizers and nebulizer masks may be suitable for the particular purpose employed, or for general use, they would not be as suitable for the purposes of the present disclosure as disclosed hereafter.

Accordingly, there is a need for nebulizer which disperses wet vapor at a high pressure and is not limited as to where it may be administered. There is also a need for a nebulizer mask which is comfortable to wear and does not enable vapor to escape onto the patient's face and hair. Such a nebulizer and nebulizer mask would provide an efficient means for lung treatment which is easy to operate and does not take a long amount of time. Such a nebulizer and nebulizer mask would also provide a lung treatment that penetrates the lungs deeper and more effectively compared to dry vapor, therefore requiring less time to complete treatment. This is because wet vapor comprises fine mist droplets which are an ideal size for reaching the lungs, in contrast dry vapor is formed from larger particles that cannot penetrate the lungs as deeply. Wet vapor is also hydrating which in turn loosens mucus, hydrates the airway lining, and reduces irritation, unlike dry vapor. Additionally, such a nebulizer and nebulizer mask would provide a lung treatment which can be utilized in any location. This would enable the patient to receive their treatment wherever is most comfortable to them, including in any position, such as laying down.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

One aspect of an example embodiment in the present disclosure is to provide a power jet nebulizer which enables an easy, quick, and comfortable means for a patient to receive their lung treatment. Another aspect of an example embodiment in the present disclosure is to provide a nebulizer mask which is comfortable to wear and does not enable vapor to escape onto the patient's face and hair. Such a power jet nebulizer and nebulizer mask will provide an efficient means for a user to receive their lung treatment, allowing the user to quickly and comfortably complete their treatment. Accordingly, the present disclosure provides a power jet nebulizer with a bottom bowl, an inverted funnel, a turbo cap, a top bowl, and a nebulizer mask which can be selectively assembled.

The power jet nebulizer is configured to convert medication and air into medicated wet vapor for a user to easily and comfortably inhale to provide treatment to their lungs. In embodiments, the power jet nebulizer may comprise medical resin, polysulfone, or any equivalent material capable of withstanding high pressure and medical sterilization. The power jet nebulizer comprises the bottom bowl configured to receive liquid medication and provide an area for air to mix with the liquid medication to convert into medicated wet vapor, the inverted funnel configured to direct the flow of air entering the power jet nebulizer to the bottom bowl to mix with the liquid medication, the turbo cap configured to guide liquid medication inserted into the nebulizer to the bottom bowl to mix with air and guide medicated wet vapor from the bottom bowl to the top bowl, the top bowl configured to receive and contain medicated wet vapor, and the nebulizer mask configured to receive and contain medicated wet vapor ready for inhaling. In embodiments, the bottom bowl is configured to house the inverted funnel to direct air and liquid medication into the bottom bowl and to direct the flow of air, liquid medication, and medicated wet vapor upward into the turbo cap. The turbo cap attaches to the bottom bowl to direct the flow of liquid medication downward into the bottom bowl and to direct the flow of medicated wet vapor upward into the top bowl. The top bowl attaches to the bottom bowl to prevent air, medicated wet vapor, and liquid medication from escaping the power jet nebulizer and to direct the flow of wet vapor to the nebulizer mask. The nebulizer mask attaches to the top bowl to receive medicated wet vapor contained in the top bowl so a user can inhale the medicated wet vapor while treating. The power jet nebulizer is easily assembled and disassembled, thereby enabling easy storage and transportation.

The bottom bowl comprises a rounded body including a base, a bulging side wall, an annular lip, and a reservoir configured to contain air, vapor, and medication. The bulging side wall interconnects the base and the annular lip. The base includes an inner surface and an outer surface opposite the inner surface. In embodiments, the outer surface is substantially planar such that the base may be placed on a surface and not fall over, thereby stabilizing the power jet nebulizer when freestanding on a surface. The bulging side wall includes an inner surface, an outer surface opposite the inner surface, an upper end, a lower end opposite the upper end, and a periphery edge disposed at the upper end. The annular lip is disposed on the upper end of the bulging side wall and extends upwardly from the periphery edge. In some embodiments, the annular lip is disposed concentrically with respect to the rounded body and the side wall. The annular lip includes a threaded inner surface, a threaded outer surface, a first end, a second end, and an opening providing access to the reservoir. The second end is adjacent to the periphery edge of the bulging side wall and the first end includes a perimeter edge defining the opening. The reservoir is defined by the inner surface of the bulging side wall and the inner surface of the base.

In embodiments, the bottom bowl further comprises a stem positioned concentrically with respect to the rounded body, the side wall, and the annular lip. The stem is configured for air to translate air exterior to the bowl therethrough into the bottom bowl. The stem includes an upper end, a lower end, and an aperture extending entirely through the stem from the lower end to the upper end. The stem extends through the base, from the outer surface to the inner surface. In this way, the stem extends entirely through the base, protrudes upwardly from the inner surface of the base toward a center of the reservoir. The lower end of the stem is configured to attach to the tubing of an oxygen tank. The aperture adjacent to the lower end comprises a diameter capable of accommodating the nozzle of the air tank. The air from the oxygen tank translates through the aperture of the stem, into the reservoir of the bottom bowl. In embodiments, the base of the rounded body further includes a recess which extends inwardly into the outer surface of the base. The lower end of the stem is housed within the recess. In this way, the base may sit flush on a flat surface, thereby enabling easy and convenient storage and use of the power jet nebulizer.

The inverted funnel comprises a conical body with a first end, a second end opposite the first end, a notched collar, and a cavity. The conical body tapers in width from the second end to the first end, such that the second end includes a greater width than the first end. The cavity extends entirely through the inverted funnel, from the first end to the second end. The notched collar is configured to direct the flow of the air, the vapor, and the medication. The notched collar is annularly disposed on the first end of the conical body and includes a notch. The notch is recessed inwardly into the notched collar. In some embodiments, the notch comprises a plurality of notches disposed around the collar. The inverted funnel further includes a raised nipple concentrically positioned at the first end of the conical body. The nipple is configured to direct vapor, medication, and air upward from the reservoir of the bottom bowl through the power jet nebulizer during use. Moreover, the nipple is configured to translate liquid medication inserted into the power jet nebulizer downward, toward the inner surface of the base. In embodiments, the nipple includes an aperture which extends entirely through the nipple, to the cavity. The aperture is configured to enable air to translate therethrough. The inverted funnel includes plurality of feet extending downwardly from the second end. The plurality of feet are configured to support the inverted funnel and vertically raise the inverted funnel off of the inner surface of the base. In this way, the plurality of feet enable air, vapor, and medication to flow and translate below the inverted funnel during use. In embodiments, the plurality of feet are annularly disposed about the cavity on the second end of the inverted funnel.

The turbo cap comprises a tubular body, an annular shoulder, a funnel, and a lip. The tubular body includes an upper end, a lower end opposite the upper end, and an internal cavity which extends entirely through the tubular body, from the upper end to the lower end. The annular shoulder is circumferentially disposed around the tubular body. The funnel extends upwardly from the upper end and includes a first end and a second end opposite the first end. The funnel tapers inwardly from the first end to the second end, such that the first end includes a greater diameter than the second end. The funnel includes an aperture which extends entirely through the funnel, from the first end to the second end. The aperture is in fluid communication with the internal cavity. The lip extends downwardly from the lower end of the annular shoulder and includes a threaded outer surface, a first end, a second end with a perimeter edge, and an opening. The perimeter edge defines the opening, the opening extends entirely through the lip, from the first end to the second end, and is in fluid communication with the internal cavity. The turbo cap includes a vent configured to direct air, vapor, and medication from the reservoir of the bottom bowl to the top bowl. In embodiments, the vent is dome shaped. The vent is disposed within the lip, adjacent to the first end. The vent includes a concave arcuate surface which guides the liquid medication laterally, towards the sides of the vent. In embodiments, the vent includes an aperture which extends entirely through the cap. This enables medication, air, and vapor to translate through the cap.

The top bowl comprises a domed body, an inlet port, an outlet port, and an internal cavity. The domed body includes an upper end, a lower end opposite the upper end, an inner surface, and an outer surface opposite the inner surface. The lower end includes a periphery edge which defines an opening. The opening provides access to the internal cavity. The internal cavity is defined by the inner surface of the domed body and is configured to house the vapor. The inner surface adjacent to the periphery edge is threaded. The inlet port is configured to receive liquid medication and is disposed on the upper end of the domed body. The inlet port protrudes upwardly from the outer surface of the domed body and includes an aperture. The aperture extends entirely through the inlet port and the domed body to the internal cavity providing access thereto. The outlet port is configured to enable vapor to translate upwardly from the internal cavity therethrough into the mask and is disposed on the upper end of the domed body. The outlet port protrudes upwardly from the domed body and includes an aperture. The aperture extends entirely through the outlet port and the domed body to the internal cavity creating a fluid communication therebetween. In embodiments, the inlet port is configured to coaxially align with the funnel of the turbo cap and nipple of the inverted funnel when in the assembled configuration to enable liquid medication poured into the inlet port to translate through the inlet port into the funnel and through the funnel to the nipple and then into the reservoir. In embodiments, the outlet port comprises a greater diameter than the inlet port to minimize the amount of vapor which may escape the power jet nebulizer via the inlet port. In embodiments, the outlet port includes a greater height than the inlet port. This is because the outlet port attaches to the mask.

The power jet nebulizer may be easily assembled and disassembled. When assembled, the inverted funnel is inserted into the reservoir of the bottom bowl via the opening of the annular lip. The plurality of feet of the inverted funnel are disposed on the inner surface of the base, the cavity of the inverted funnel receives and encompasses the upper end of the stem. The cavity of the inverted funnel includes a height and width greater than the stem so the stem does not encompass the entirety of the cavity This enables air to translate through the stem, into the cavity, downward through the cavity, and into the reservoir. The threaded outer surface of the lip of the turbo cap engages the threaded inner surface of the annular lip of the bottom bowl. This enables the turbo cap to selectively attach to the bottom bowl. The threaded inner surface of the top bowl engages the threaded outer surface of the annular lip of the bottom bowl. This enables the top bowl to selectively attach to the bottom bowl. In this way, the top bowl houses the turbo cap and the bottom bowl houses the inverted funnel. When assembled, the lower end of the tubular body is disposed flush on the perimeter edge of the annular lip of the bottom bowl and the lower end of the top bowl is disposed flush on the periphery edge of the bulging side wall of the bottom bowl.

The power jet nebulizer further includes a longitudinal axis which extends vertically along the center of the power jet nebulizer. The aperture of the stem, the aperture of the nipple, the aperture of the cap, the internal cavity of the tubular body of the turbo cap, the aperture of the funnel, and the aperture of the inlet port are vertically aligned with the longitudinal axis when the power jet nebulizer is in the assembled configuration. In this way, the aperture of the stem, the aperture of the nipple, the aperture of the cap, the internal cavity of the tubular body, the aperture of the funnel, and the aperture of the inlet port are vertically aligned with each other and are in fluid communication when the power jet nebulizer is in the assembled configuration. This enables medication, air, and vapor to translate through the power jet nebulizer.

In embodiments, the periphery edge of the bulging side wall includes a gasket. The gasket is configured to seal the bottom bowl and the top bowl when the power jet nebulizer is in the assembled configuration, thereby preventing air, medication, and vapor from escaping the power jet nebulizer when in use. In embodiments, the lower end of the annular shoulder includes a gasket. The gasket is configured to seal the turbo cap and the bottom bowl when the power jet nebulizer is in the assembled configuration, thereby preventing air, medication, and vapor from escaping the power jet nebulizer when in use.

The power jet nebulizer is configured to accommodate high pressure due to the material which the power jet nebulizer comprises. In embodiments, the power jet nebulizer is configured to accommodate pressure within the range of 8 psi-35 psi. This enables air to translate through the power jet nebulizer to provide a faster means to receive treatment compared to traditional nebulizers. Moreover, this enables air to quickly and efficiently break down liquid medication residing in the reservoir of the bottom bowl.

In embodiments, the power jet nebulizer further comprises a nebulizer mask. The nebulizer mask includes a body, a lip, and a joint. The body is configured to cover a user's nose and mouth and includes a perimeter edge, an inner surface, an outer surface opposite the inner surface, a reservoir, an upper end, and a lower end. The reservoir is configured to receive medicated wet vapor from the top bowl. The perimeter edge includes a face seal configured to seal the mask against the user's face. The lip is disposed on the lower end of the body and includes a first end, a second end, and a side wall which extends between the first end and the second end. The first end is adjacent to the body and the side wall extends outwardly, away from the outer surface of the body. In embodiments, the side wall is tubular. The lip further includes a retaining rim and an aperture. The retaining rim is configured to seal where the lip and the joint meet, thereby preventing medicated vapor from escaping the mask. The aperture extends entirely through the lip, from the first end to the second end, and through the body, from the outer surface to the inner surface, thereby providing access to the reservoir. In embodiments, the retaining rim is annularly disposed about the aperture, adjacent to the first end of the lip. The joint is configured to interconnect the outlet port and the mask, creating a fluid communication therebetween and enabling the medicated vapor to translate from the power jet nebulizer in the mask for the user to inhale. The joint includes a base, a cylindrical body, and an aperture. The base includes a first end and a second end opposite the first end. In embodiments, the base is circular in shape. The cylindrical body extends downwardly from the second end of the base, past the lip. The aperture extends entirely through the joint, through the cylindrical body and the base. The aperture provides access to the reservoir. In embodiments, the first end comprises a ball joint which enables the joint to rotate about the lip. This enables the user to administer their treatment from any position, thereby promoting easy, comfortable, and convenient use. A plurality of fasteners are coupled to the outer surface of the body. A strap interconnects the plurality of fasteners and is configured to fasten the mask to the user. The strap is flexible and may stretch around the user's head.

In operation of embodiments, the power jet nebulizer converts liquid medication into medicated vapor using air introduced into the power jet nebulizer. The user first assembles the power jet nebulizer and attaches the mask to the outlet port. The user then inserts the medication into the aperture of the inlet port. The medication translates through the inlet port into the internal cavity of the top bowl. The medication continues to translate downward through the aperture of the funnel of the turbo cap. The medication then translates from the aperture of the funnel to the internal cavity of the tubular body of the turbo cap. The medication then contacts the vent of the turbo cap and translates outwardly, towards the sides of the cap. In this way, the medication is directed around the cap, towards the inverted funnel. The medication contacts the first end of the inverted funnel and translates downwardly, through the notched collar. The notch directs the medication towards the second end of the inverted funnel. The medication continues to translate downward until it contacts the inner surface of the base. Next, the user turns on the oxygen tank thereby enabling air to travel from the oxygen tank to the stem. The air translates through the aperture of the stem, into the cavity of the inverted funnel. The air translates both downwardly through the cavity of the inverted funnel along the stem towards the inner surface of the base and upwardly through the aperture of the nipple. In this way, air fills the reservoir and begins to mix with the medication. This causes the medication to translate with the air. The air and the medication translate in a circular direction, around the reservoir, thereby enabling the air and the medication to mix together. The high pressure of the air causes the mixture to translate upwardly, about the inverted funnel. Additionally, the air contacts the medication at a high velocity, thereby causing the medication to break down into medicated vapor. The medicated vapor is cold, soothing, easier to inhale, and penetrates the lungs easier. This enables a more comfortable treatment for the user. The mixture continues to translate upward until the mixture contacts the notched collar. The mixture is directed through the notch towards the opening of the lip of the turbo cap. The mixture continues to translate through the opening of the lip, the internal cavity of the tubular body, and the aperture of the funnel. The air continues to break apart the medication, thereby converting the medication into the medicated vapor. The medicated vapor translates into the internal cavity of the top bowl. The high pressure of the air translates the medicated vapor towards and through the aperture of the outlet port into the mask. The user then inhales the medicated vapor until their treatment is complete.

In embodiments, the power jet nebulizer further comprises a mask coupler to accommodate an industry standard mask. The mask coupler enables the vapor to translate between the power jet nebulizer and the industry standard mask. The mask coupler comprises a tubular body with a first end, a second end, and an aperture. The aperture extends entirely through the mask coupler, from the first end to the second end. The first end of the mask coupler selectively attaches to the industry standard mask. The second end of the mask coupler selectively attaches to the outlet port of the top bowl via friction fit. In embodiments, the mask coupler comprises a diameter smaller than the diameter of the outlet port. In this way, the second end of the mask coupler may be inserted into the outlet port. This enables the mask coupler to be in fluid communication with the outlet port, thereby enabling medicated vapor to translate from the power jet nebulizer to the industry standard mask.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

Figure 1:
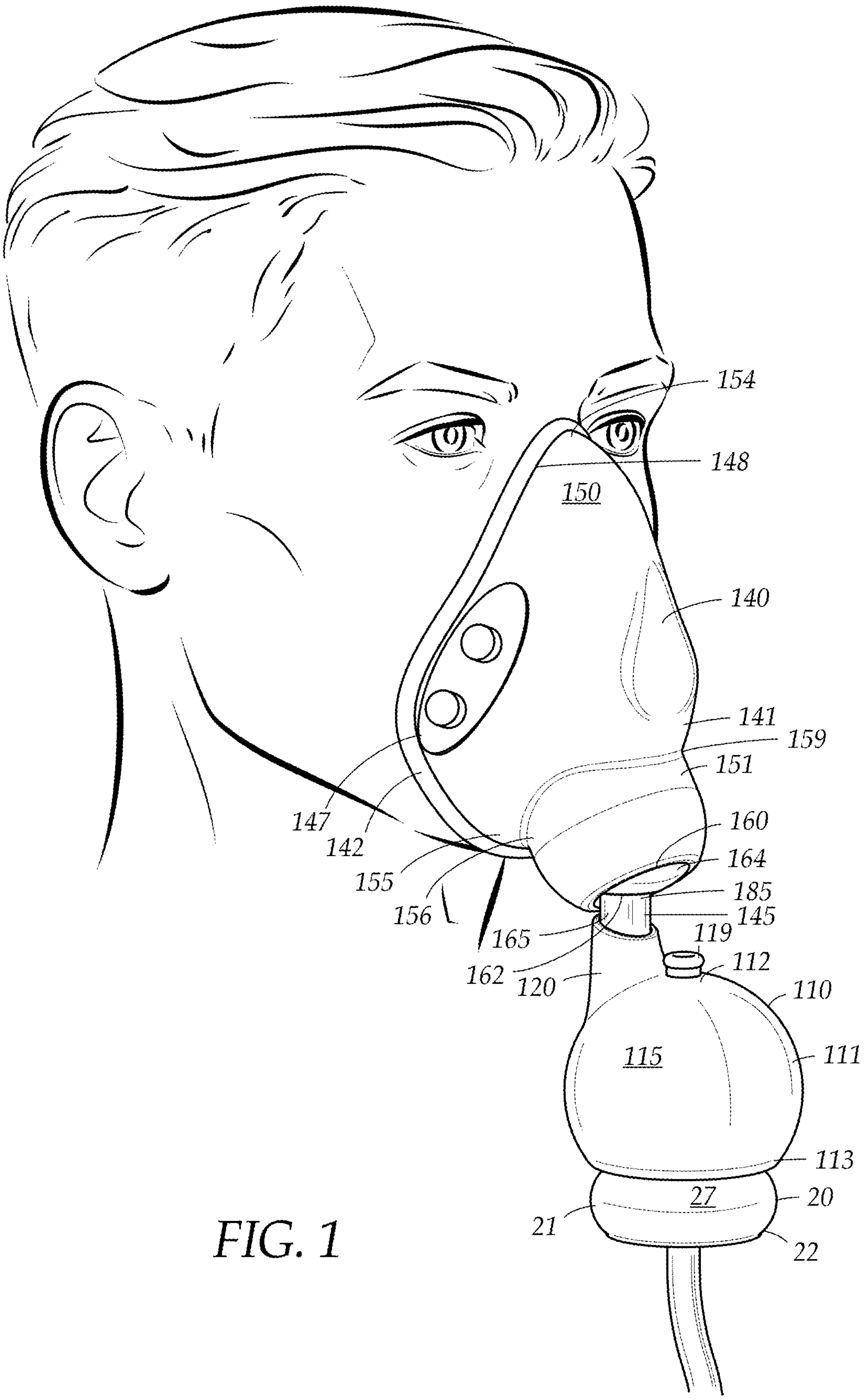
FIG. 1 shows a perspective view of the power jet nebulize, illustrating the power jet nebulizer and the mask in use in accordance with one embodiment of the present disclosure.
Figure 2:
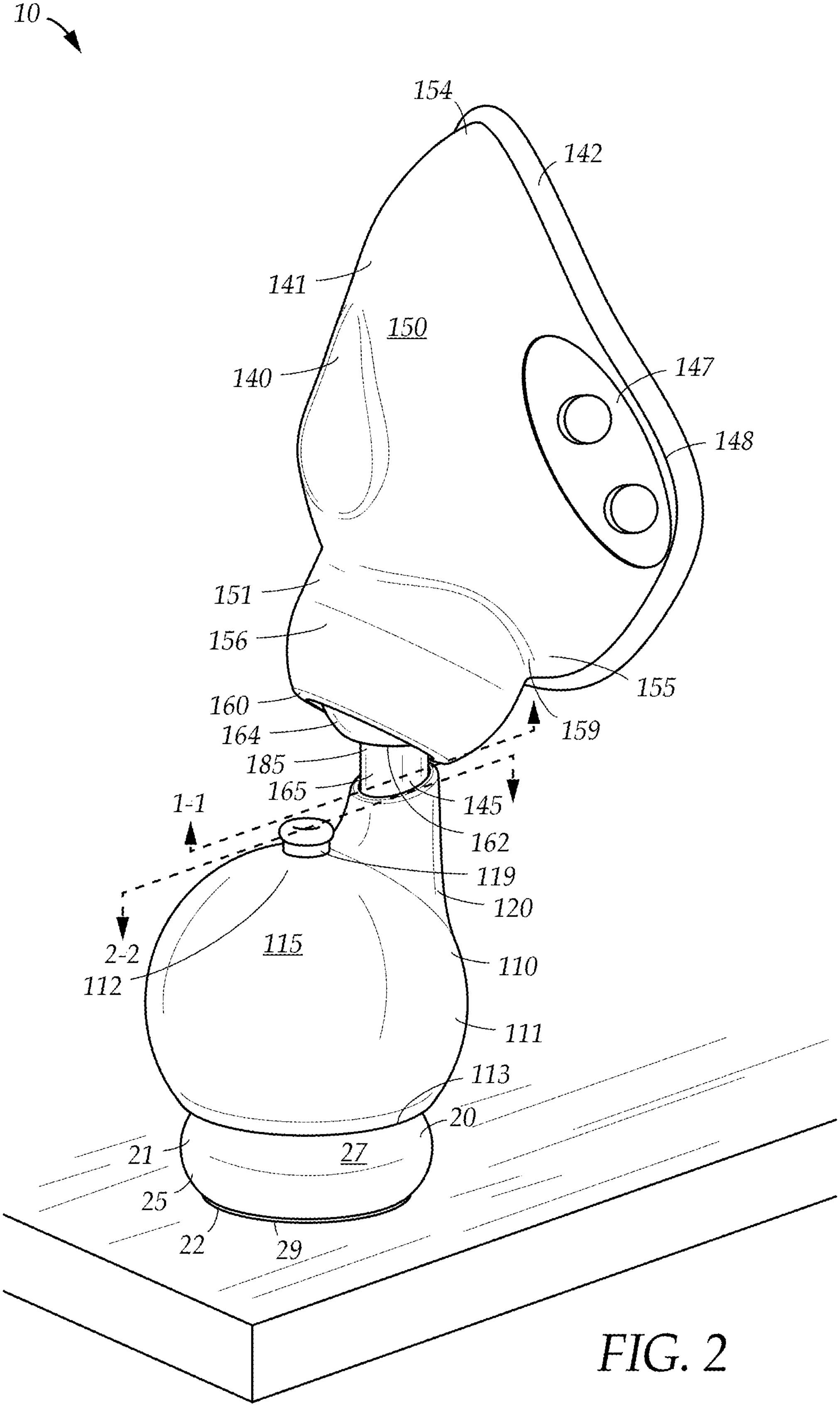
FIG. 2 shows a perspective view of the power jet nebulizer, illustrating the power jet nebulizer and the mask in the assembled configuration in accordance with one embodiment of the present disclosure.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION

As discussed above, medical professionals have long recognized the importance of nebulizer treatments. Nebulizers are typically used to treat lung diseases and respiratory conditions. It is critical that nebulizers are easy, quick, and comfortable to use. Traditional nebulizers frequently dispense dry vapor which irritates the patient's airway and takes a longer time to penetrate the lungs. These nebulizers typically include limited air pressure which causes the treatment to take a longer duration. These nebulizers also commonly operate by being plugged into an outlet, thereby limiting where a patient can complete their treatment. Moreover, traditional nebulizer masks frequently are uncomfortable, easily dislodge from the tubing connected to the nebulizer, and include holes which release vapor onto the patient's face and hair. While various attempts have been made to address these issues, these solutions are impractical. The embodiments herein address these issues and other issues.

Referring now to FIG. 1, FIG. 2, FIG. 3, FIG. 4, and FIG. 7, the present disclosure provides a power jet nebulizer 10 configured to convert medication and air into medicated wet vapor. The power jet nebulizer 10 provides an efficient, quick, and comfortable means for a patient to complete their lung treatment. The power jet nebulizer 10 may comprise medical resin, polysulfone, or any equivalent material capable of withstanding high pressure and medical sterilization. The power jet nebulizer 10 comprises a bottom bowl 20 configured to receive liquid medication and provide an area for air to mix with the liquid medication to convert into medicated wet vapor, an inverted funnel 60 configured to direct the flow of air entering the power jet nebulizer 10 to the bottom bowl 20 to mix with the liquid medication, a turbo cap 80 configured to guide liquid medication inserted into the nebulizer 10 to the bottom bowl 20 to mix with air and guide medicated wet vapor upwardly from the bottom bowl 20, a top bowl 110 configured to receive and contain medicated wet vapor, and a nebulizer mask 140 configured to receive and contain medicated wet vapor ready for inhaling. In embodiments, the bottom bowl 20 is configured to house the inverted funnel 60 to direct air and liquid medication into the bottom bowl and to direct the flow of air, liquid medication, and medicated wet vapor upward into the turbo cap 80. The turbo cap 80 attaches to the bottom bowl 20 to direct the flow of liquid medication downward into the bottom bowl 20 and to direct the flow of medicated wet vapor upward into the top bowl 110. The top bowl 110 attaches to the bottom bowl 20 to prevent air, medicated wet vapor, and liquid medication from escaping the power jet nebulizer 10 and to direct the flow of medicated wet vapor to the nebulizer mask 140. The nebulizer mask 140 attaches to the top bowl 110 to receive medicated wet vapor contained in the top bowl 110 so a user can inhale the medicated wet vapor while treating. The power jet nebulizer 10 is easily assembled and disassembled, thereby enabling easy storage and transportation.

The bottom bowl 20 comprises a rounded body 21 including a base 22, a bulging side wall 25, an annular lip 31, and a reservoir 38 configured to contain air, vapor, and medication. The bulging side wall 25 interconnects the base 22 and the annular lip 31. The base 22 includes an inner surface 23 and an outer surface 24 opposite the inner surface 23. In embodiments, the outer surface 24 is substantially planar. In this way, the base 22 may be placed on a surface and will not fall over, thereby stabilizing the power jet nebulizer 10 when freestanding on a surface. The bulging side wall 25 includes an inner surface 26, an outer surface 27 opposite the inner surface 26, an upper end 28, a lower end 29 opposite the upper end 28, and a periphery edge 30 disposed at the upper end 28. The annular lip 31 is disposed on the upper end 28 of the bulging side wall 25 and extends upwardly from the periphery edge 30. In some embodiment, the annular lip 31 is disposed concentrically with respect to the rounded body 21 and side wall 25. The annular lip 31 includes a threaded inner surface 32, a threaded outer surface 33 opposite the threaded inner surface 32, a first end 36, a second end 37 opposite the first end 36, and an opening 35 providing access to the reservoir 38. The second end 37 is adjacent to the periphery edge 30 of the bulging side wall 25 and the first end 36 includes a perimeter edge 34 defining the opening 35. The reservoir 38 is defined by the inner surface 26 of the bulging side wall 25 and the inner surface 23 of the base 22.

In embodiments, the bottom bowl 20 further includes a stem 39 positioned concentrically with respect to the rounded body 21, side wall 25, and annular lip 31. The stem 39 is configured to translate air exterior to the bowl therethrough into the bottom bowl 20. The stem 39 comprises an upper end 40, a lower end 41 opposite the upper end 40, and an aperture 42 which extends through the stem 39 from the lower end 41 to the upper end 40. The stem 39 extends through the base 22, from the outer surface 24 to the inner surface 23. In this way, the stem 39 protrudes downwardly from the outer surface 24 of the base 22, through the base 22, and protrudes upwardly from the inner surface 23 of the base 22 toward a center of the reservoir 38. The lower end 41 of the stem 39 is configured to attach to the tubing of an oxygen tank. The aperture 42 adjacent to the lower end 41 comprises a diameter capable of accommodating the nozzle of the air tank. The air from the oxygen tank translates through the aperture 42 of the stem 39 into the reservoir 38 of the bottom bowl 20. In some embodiments, the base 22 includes a recess 43 which extends inwardly into the outer surface 24. In embodiments, the lower end 41 of the stem 39 is positioned at the center of the recess 43. In embodiments, the lower end 41 of the stem 39 includes a length less than the depth of the recess 43. In this way, the lower end 41 of the stem does not extend past the outer surface 24 of the base 22. This enables the base 22 to sit flush on a flat surface which promotes easy storage and use of the power jet nebulizer 10.

The inverted funnel 60 comprises a conical body 61 with a first end 62, a second end 63 opposite the first end 62, a notched collar 64, and a cavity 68. The conical body 61 tapers in width from the second end 63 to the first end 62, such that the second end 63 includes a greater width than the first end 62. The cavity 68 extends entirely through the inverted funnel 60, from the first end 62 to the second end 63. The notched collar 64 is configured to direct the flow of air, vapor, and medication. The notched collar 64 is annularly disposed on the first end 62 of the conical body 61 and comprises a notch 70. The notch 70 is recessed inwardly into the notched collar 64. In some embodiments, the notch 70 comprises a plurality of notches 70 disposed around the collar 64. The inverted funnel 60 further includes a raised nipple 65 concentrically positioned at the first end 62 of the conical body 61. The nipple 65 is configured to direct vapor, medication, and air upward from the reservoir 38 of the bottom bowl 20 through the power jet nebulizer 10 during use. Moreover, the nipple 65 is configured to translate liquid medication inserted into the power jet nebulizer 10 downward, toward the inner surface 23 of the base 22. In embodiments, the nipple 65 includes an aperture 66 which extends entirely through the nipple 65, to the cavity 68. The aperture 66 is configured to enable air to translate therethrough. The inverted funnel 60 includes a plurality of feet 69 configured to support the inverted funnel 60 and vertically raise the inverted funnel 60 off of the inner surface 23 of the base 22. In this way, the plurality of feet 69 enable air, vapor, and medication to flow and translate below the inverted funnel 60 during use. In embodiments, the plurality of feet 69 are annularly disposed about the cavity 68.

The turbo cap 80 comprises a tubular body 81, an annular shoulder 97, a funnel 85, and a lip 89. The tubular body 81 includes an upper end 82, a lower end 83 opposite the upper end 82, and an internal cavity 84. The internal cavity 84 extends entirely through the tubular body 81, from the upper end 82 to the lower end 83. The annular shoulder 97 is circumferentially disposed around the tubular body 81 and includes an upper end 98 and a lower end 99 opposite the upper end 98. The funnel 85 extends upwardly from the upper end 82 of the tubular body 81 and includes a first end 86, a second end 87, and an aperture 88. The funnel 85 tapers inwardly from the first end 86 to the second end 87, such that the first end 86 includes a greater diameter than the second end 87. The aperture 88 extends entirely through the funnel 85, from the first end 86 to the second end 87. The aperture 88 is in fluid communication with the internal cavity 84. The lip 89 extends downwardly from the lower end 99 of the annular shoulder 97 and includes a threaded outer surface 90, a first end 91, a second end 92, and an opening 94. The second end 92 includes a perimeter edge 93 which defines the opening 94. The opening 94 extends entirely through the lip 89, from the first end 91 to the second end 92. The opening 94 provides access to the internal cavity 84. The turbo cap 80 further includes a vent 95 configured to direct air, medication, and vapor from the reservoir 38 of the bottom bowl 20 to the top bowl 110. In embodiments, the vent 95 is dome shaped. The vent 95 is disposed within the lip 89, adjacent to the first end 91. The vent 95 includes a concave arcuate surface which guides the liquid medication laterally, towards the sides of the vent 95. In embodiments, the vent 95 includes an aperture 96 which extends entirely through the vent 95. This enables medication, air, and vapor to translate through the vent 95.

The top bowl 110 comprises a domed body 111, an inlet port 119, an outlet port 120, and an internal cavity 118. The domed body 111 includes an upper end 112, a lower end 113 opposite the upper end 112, an inner surface 114, an outer surface 115 opposite the inner surface 114, and an opening 117. The lower end 113 of the domed body 111 includes a periphery edge 116 which defines the opening 117. The opening 117 provides access to the internal cavity 118. The internal cavity 118 is configured to house the vapor and is defined by the inner surface 114 of the domed body 111. The inner surface 114 adjacent to the periphery edge 116 is threaded. The inlet port 119 is configured to receive liquid medication therethrough and is disposed on the upper end 112 of the domed body 111. The inlet port 119 protrudes upwardly from the domed body 111 and includes an aperture 121. The aperture 121 extends entirely through the inlet port 119 and the domed body 111 to the internal cavity 118 providing access thereto. The outlet port 120 is configured to enable vapor to translate upwardly from the internal cavity 118 therethrough into the mask 140 and is disposed on the upper end 112 of the domed body 111. The outlet port 120 protrudes upwardly from the domed body 111 and includes an aperture 122. The aperture 122 extends entirely through the outlet port 120 and the domed body 111 to the internal cavity 118 creating a fluid communication therebetween. In embodiments, the inlet port 119 and the outlet port 120 are offset from each other. In some embodiments, the inlet port 119 is disposed at the center of the domed body 111. In embodiments, the inlet port 119 is configured to coaxially align with the funnel 85 of the turbo cap 80 and nipple 65 of the inverted funnel 60 when in the assembled configuration to enable liquid medication poured into the inlet port 119 to translate through the inlet port 119 into the funnel 85 and through the funnel 85 to the nipple 65 and then into the reservoir 38. In embodiments, the outlet port 120 comprises a greater diameter than the inlet port 119 to minimize the amount of vapor which may escape the power jet nebulizer 10 via the inlet port 119. In embodiments, the outlet port 120 includes a greater height than the inlet port 119. This is because the outlet port 120 attaches to the mask 140.

The power jet nebulizer 10 may be easily assembled and disassembled. When assembled, the inverted funnel 60 is inserted into the reservoir 38 of the bottom bowl 20 via the opening 35 of the annular lip 31. The plurality of feet 69 of the inverted funnel 60 contact the inner surface 23 of the base 22. The cavity 68 of the inverted funnel 60 receives and encompasses the upper end of the stem 39. The cavity 68 includes a greater height and width than the stem 39 so the stem 39 does not encompass the entirety of the cavity 68. This enables air to translate through the stem 39, into the cavity 68, downward through the cavity, and into the reservoir 38. The threaded outer surface 90 of the lip 89 of the turbo cap 80 engages the threaded inner surface 32 of the annular lip 31 of the bottom bowl 20. This enables the turbo cap 80 to selectively attach to the bottom bowl 20. The threaded inner surface 114 of the top bowl 110 engages the threaded outer surface 33 of the annular lip 31 of the bottom bowl 20. This enables the top bowl 110 to selectively attach to the bottom bowl 20. In this way, the inverted funnel 60 and the turbo cap 80 are housed within the reservoir 38 of the bottom bowl 20 and the internal cavity 118 of the top bowl 110. In embodiments, when assembled, the lower end 83 of the annular shoulder 97 of the turbo cap 80 is disposed flush on the perimeter edge 34 of the annular lip 31 of the bottom bowl 20. In embodiments, the lower end 113 of the top bowl 110 is disposed flush on the periphery edge 30 of the bulging side wall 25 of the bottom bowl 20.

The power jet nebulizer 10 further includes a longitudinal axis 11 which extends vertically along the center of the power jet nebulizer 10. The aperture 42 of the stem 39, the aperture 66 of the nipple 65, the aperture 96 of the vent 95, the internal cavity 84 of the tubular body 81 of the turbo cap 80, the aperture 88 of the funnel 85, and the aperture 121 of the inlet port 119 are vertically aligned with the longitudinal axis 11. In this way, the aperture 42 of the stem 39, the aperture 66 of the nipple 65, the aperture 96 of the vent 95, the internal cavity 84 of the tubular body 81 of the turbo cap 80, the aperture 88 of the funnel 85, and the aperture 121 of the inlet port 119 are vertically aligned and in fluid communication with each other when the power jet nebulizer 10 is assembled. This enables medication, air, and vapor to translate through the power jet nebulizer 10.

In embodiments, the periphery edge 30 of the bulging side wall 25 includes a gasket. The gasket is configured to seal the bottom bowl 20 and the top bowl 110 when the power jet nebulizer 10 is in the assembled configuration. This prevents air, medication, and vapor from escaping the power jet nebulizer 10 during use. In embodiments, the lower end 99 of the annular shoulder 97 includes a gasket. The gasket is configured to seal the turbo cap 80 and the bottom bowl 110 when the power jet nebulizer 10 is in the assembled configuration. This prevents air, medication, and vapor from escaping the power jet nebulizer 10 during use.

The power jet nebulizer 10 is configured to accommodate high pressure due to the material which the power jet nebulizer 10 comprises. In embodiments, the power jet nebulizer is configured to accommodate pressure within the range of 8 psi-35 psi. This enables air to translate through the power jet nebulizer 10 at a higher velocity, thereby enabling the power jet nebulizer 10 to provide a faster means to receive treatment compared to traditional nebulizers. Moreover, this enables air to quickly and efficiently break down liquid medication residing in the reservoir 38 of the bottom bowl 20.

Figure 6:
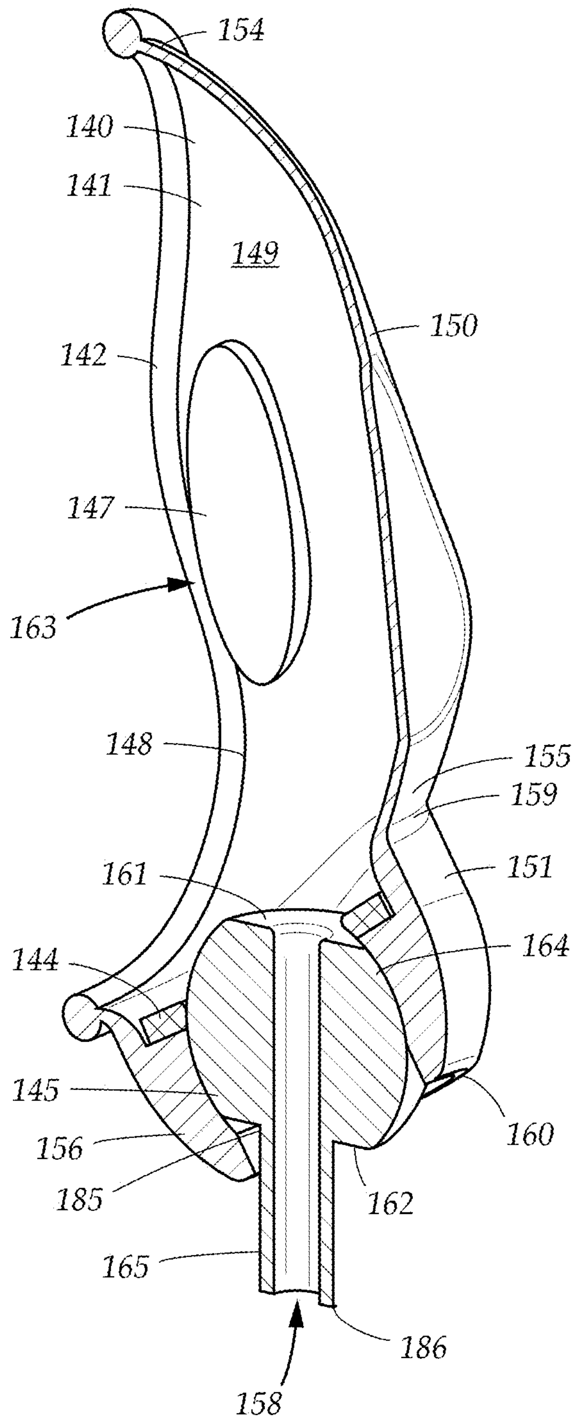
FIG. 6 shows a perspective cross-sectional view of the mask taken along line 1-1 of FIG. 2, illustrating the retaining rim and the joint of the mask in accordance with one embodiment of the present disclosure.

Referring now to FIG. 6, while continuing to refer to FIG. 1, FIG. 2, FIG. 3, and FIG. 4, the mask 140 includes a body 141, a lip 151, and a joint 145. The body 141 is configured to cover the user's nose and mouth and includes a perimeter edge 148, an inner surface 149, an outer surface 150 opposite the inner surface 149, a reservoir 163, an upper end 154, and a lower end 155 opposite the upper end 154. The reservoir 163 is configured to receive medicated wet vapor from the top bowl. The perimeter edge 148 includes a face seal 142 configured to seal the mask 140 against the user's face. In this way, medicated vapor cannot leak out of the mask 140 onto the user's face, hair, and clothes during use. This also promotes efficiency as all of the medicated vapor can be inhaled by the user. The lip 151 is disposed on the lower end 155 of the body 141 and extends outwardly, away from the body 141. The lip 151 includes a first end 159, a second end 160 opposite the first end 159, and a side wall 156 which extends between the first end 159 and the second end 160. In embodiments, the side wall 156 is tubular. In embodiments, the side wall 156 curves inwardly at the second end 160 to accommodate the joint 145. The first end 159 is adjacent to the body 141 and the side wall 156 extends outwardly, away from the outer surface 150 of the body 141. The lip 151 further includes a retaining rim 144 and an aperture 166. The retaining rim 144 is configured to seal where the lip 151 and the joint 145 meet, thereby preventing medicated vapor from escaping the mask 140. The aperture

166 extends entirely through the lip 151, from the first end 159 to the second end 160, through the body 141. In this way, the aperture 166 provides access to the reservoir 163. In embodiments, the retaining rim 144 is annularly disposed about the aperture, adjacent to the first end 159 of the lip 151. The joint 145 is configured to interconnect the outlet port 120 and the mask 140, creating a fluid communication therebetween and enabling the medicated vapor to translate from the power jet nebulizer 10 to the mask 140 for the user to inhale. The joint 145 includes a base 164, a cylindrical body 165, and an aperture 158. The base 164 is disposed within the aperture 166 of the lip 151 and includes a first end 161 and a second end 162 opposite the first end 161. In embodiments, the base 164 is circular in shape. In embodiments, the base 164 comprises a ball joint. In embodiments, the aperture 166 of the lip 151 comprises substantially the same shape and size of the base 164. This enables the base 164 to rotate and pivot within the aperture 166 of the lip 151, thereby enabling the user to administer their treatment from any position. This promotes easy, comfortable, and convenient use. The cylindrical body 165 extends outwardly from the second end 162 of the base 164. The cylindrical body 165 comprises an upper end 185 and a lower end 186 opposite the upper end 185. The aperture 158 extends entirely through the joint 145, from the lower end 186 of the cylindrical body 165 to the first end 161 of the base 164. The aperture 158 provides access to the reservoir 163. In embodiments, the cylindrical body 165 comprises a smaller diameter than the aperture 122 of the outlet port 120. In this way, the cylindrical body 165 may selectively attach to the outlet port 120 via a friction fit. Medicated vapor translates through the outlet port 120 into the aperture 158, then into the reservoir 163. In embodiments, the cylindrical body 165 includes a vent for excess vapor to exit therethrough. In embodiments, the user holds the mask to their face. In embodiments, a plurality of fasteners 147 are coupled to the outer surface 150 of the body 141. A strap configured to flexibly stretch around the user's head interconnects the plurality of fasteners.

Figure 3:
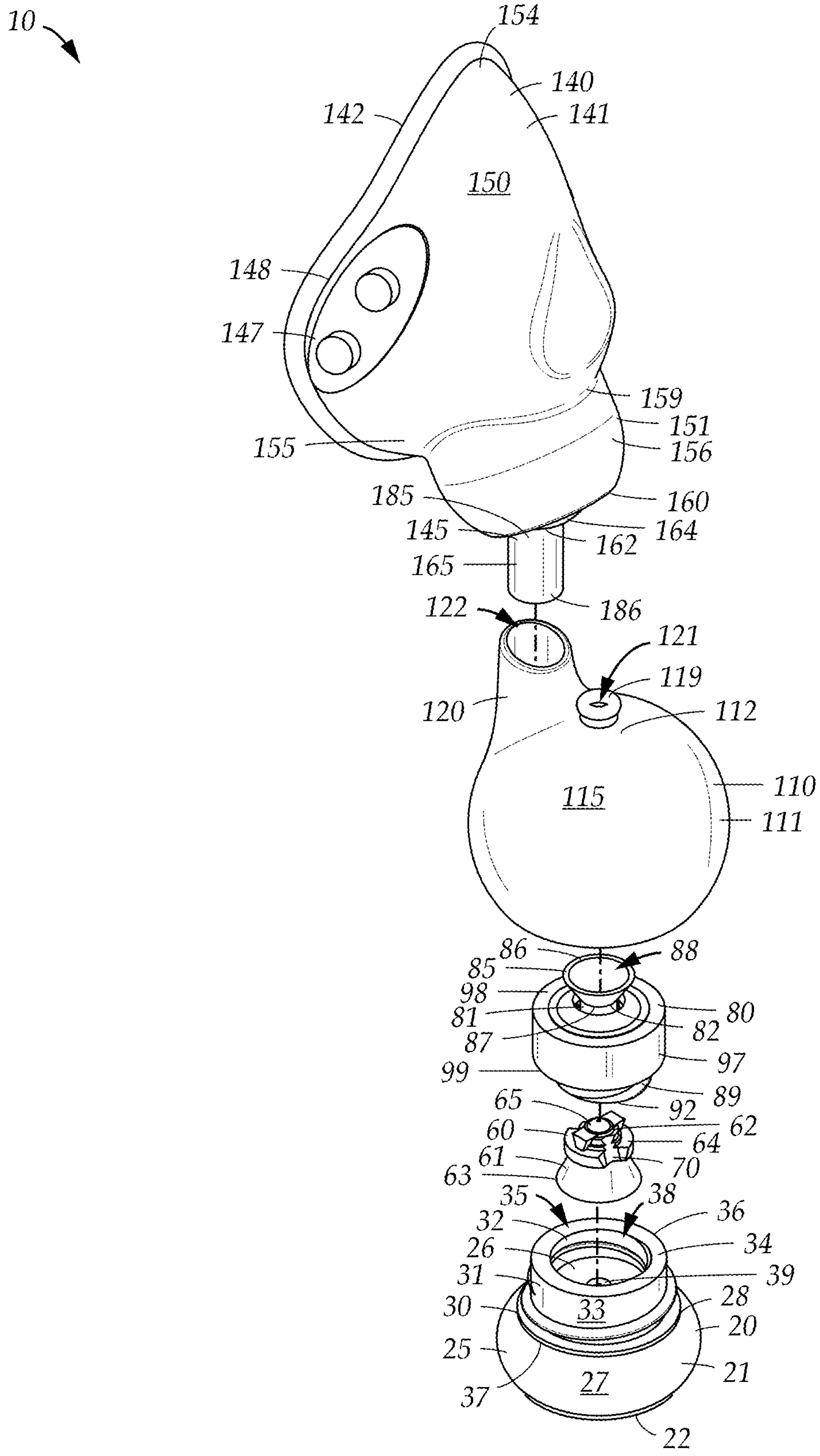
FIG. 3 shows an exploded view of the power jet nebulizer, illustrating a top view of the individual components of the power jet nebulizer and the mask in accordance with one embodiment of the present disclosure.
Figure 4:
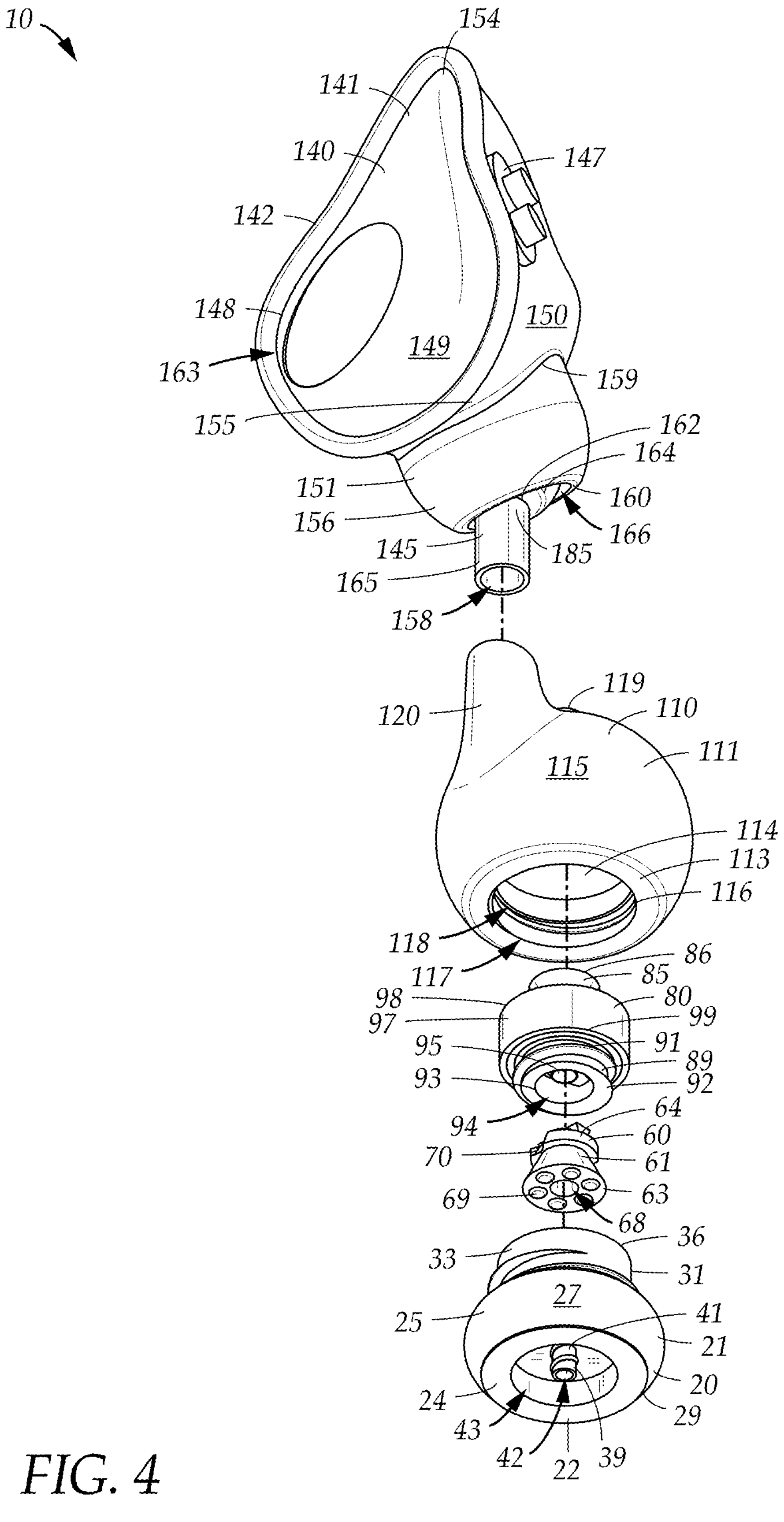
FIG. 4 shows an exploded view of the power jet nebulizer, illustrating a bottom view of the individual components of the power jet nebulizer and the mask in accordance with one embodiment of the present disclosure.
Figure 7:
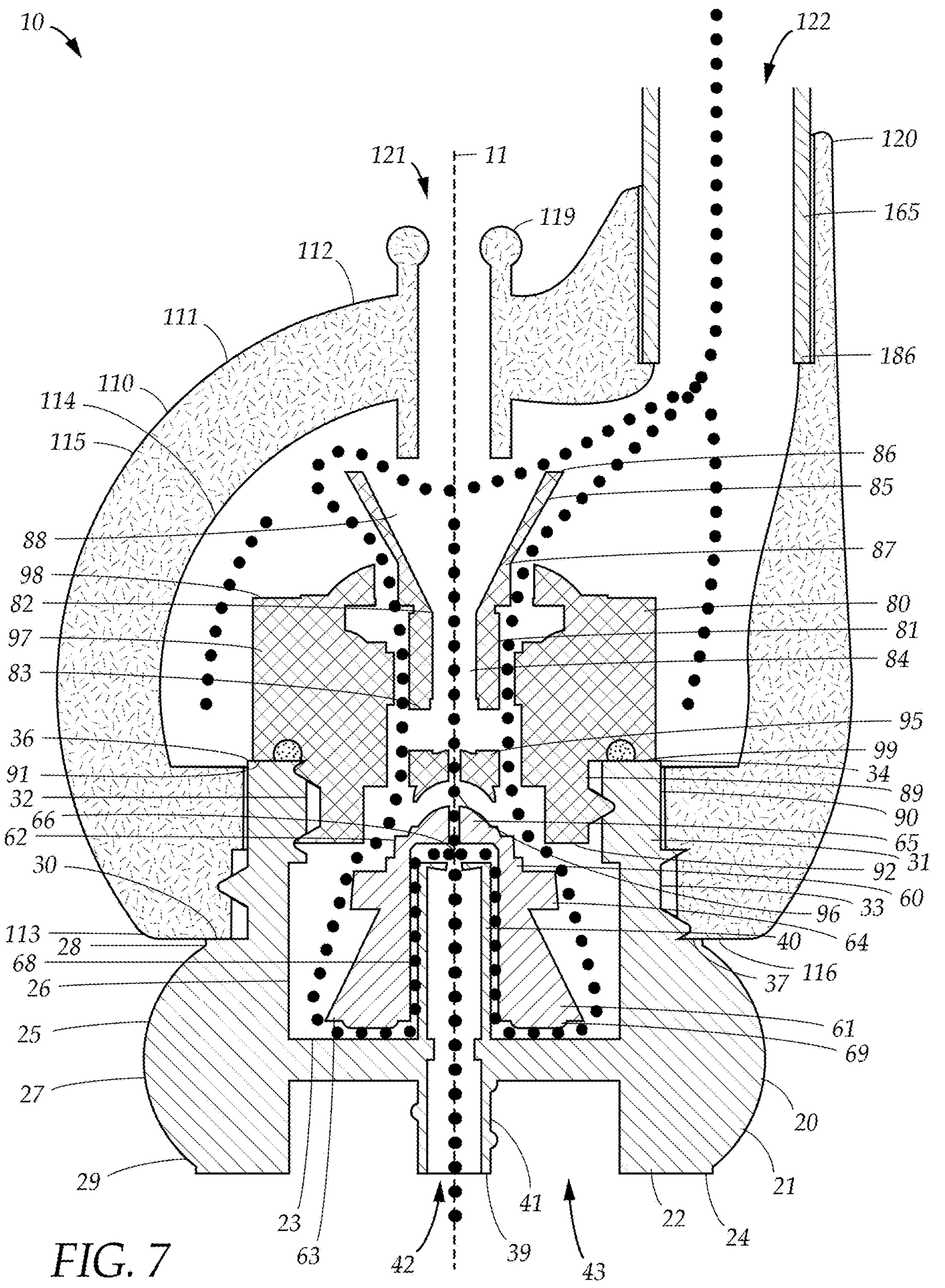
FIG. 7 shows a cross-sectional view of the power jet nebulizer taken along line 2-2 of FIG. 2, illustrating the interrelationship of the components of the power jet nebulizer in the assembled configuration and further illustrating how the air and the vapor travel from the stem to the mask in accordance with one embodiment of the present disclosure.
Figure 8:
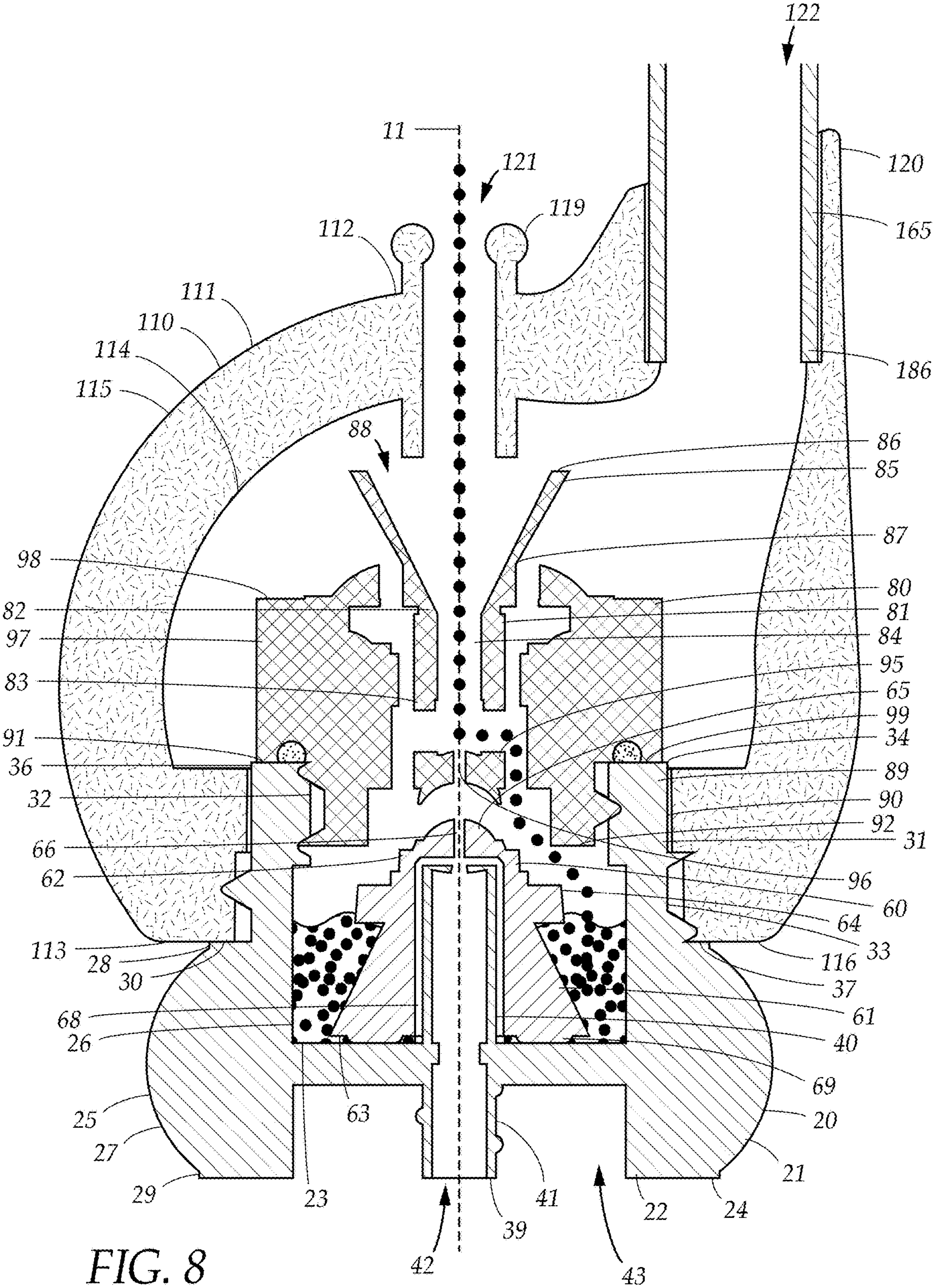
FIG. 8 shows a cross-sectional view of the power jet nebulizer taken along line 2-2 of FIG. 2, illustrating the interrelationship of the components of the power jet nebulizer in the assembled configuration and further illustrating how the medication travels from the inlet port to the base of the bottom bowl in accordance with one embodiment of the present disclosure.

Referring now to FIG. 7 and FIG. 8, while continuing to refer to FIG. 3 and FIG. 4, in operation of embodiments, the power jet nebulizer 10 converts liquid medication into medicated vapor using air introduced into the power jet nebulizer 10. The user first assembles the power jet nebulizer and attaches the mask 140 to the outlet port 120. The user then inserts liquid medication into the aperture 121 of the inlet port 119. The medication translates through the inlet port 119 into the internal cavity 118 of the top bowl 110. The medication continues to translate downward through the aperture 88 of the funnel 85 of the turbo cap 80. The medication then translates from the aperture 88 of the funnel 85 to the internal cavity 84 of the tubular body 81 of the turbo cap 80. The medication then contacts the vent 95 of the turbo cap 80 and translates outwardly, towards the sides of the vent 95. In this way, the medication is directed around the vent 95 towards the inverted funnel 60. The medication contacts the first end 62 of the inverted funnel 60 and translates downwardly, through the notched collar 64. The notch 70 directs the medication towards the second end 63 of the inverted funnel 60. The medication continues to translate downward until it contacts the inner surface 23 of the base 22. Next, the user turns on the oxygen tank thereby enabling air to travel from the oxygen tank to the stem 39. The air translates through the aperture 42 of the stem 39, into the cavity 68 of the inverted funnel 60. The air translates both downwardly through the cavity 68 of the inverted funnel 60 along the stem 39 towards the inner surface 23 of the base 22 and upwardly through the aperture 66 of the nipple 65. In this way, the air fills the reservoir 38 and begins to mix with the medication. This causes the medication to translate with the air. The air and the medication translate in a circular direction, around the reservoir 38, thereby enabling the air and the medication to mix together. The high pressure of the air causes the mixture to translate upwardly, about the inverted funnel 60. Additionally, the air contacts the medication at a high velocity, thereby causing the medication to break down into medicated vapor. The medicated vapor is cold, soothing, easier to inhale, and penetrates the lungs easier. This enables a more comfortable treatment for the user. The mixture continues to translate upward until the mixture contacts the notched collar 64. The mixture is directed through the notch 70 towards the opening 94 of the lip 89 of the turbo cap 80. The mixture continues to translate through the opening 94 of the lip 89, the internal cavity 84 of the tubular body 81, and the aperture 88 of the funnel 85. The air continues to break apart the medication, thereby converting the medication into the medicated vapor. The medicated vapor translates into the internal cavity 118 of the top bowl 110. The high pressure of the air translates the medicated vapor towards and through the aperture 122 of the outlet port 120 into the mask 140. The user then inhales the medicated vapor until their treatment is complete.

Figure 5:
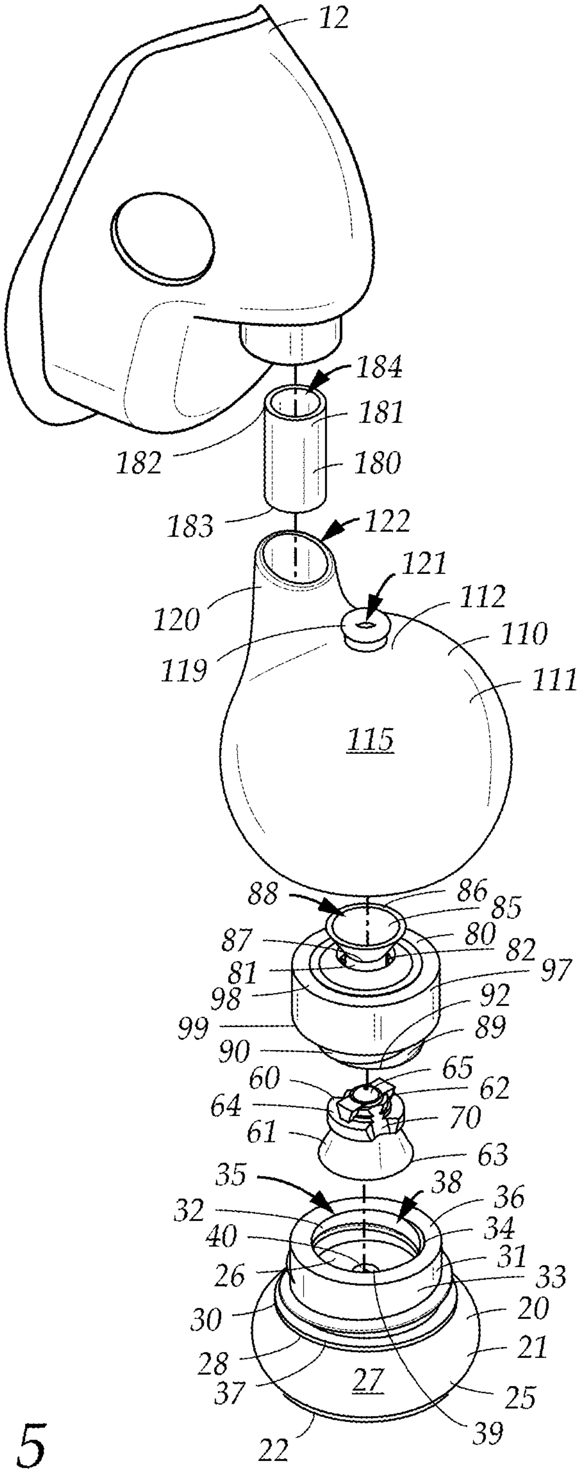
FIG. 5 shows an exploded view of the power jet nebulizer, illustrating a top view of the individual components of the power jet nebulizer, the mask coupler, and the industry standard mask and the way in which they assemble in accordance with one embodiment of the present disclosure.

Referring now to FIG. 4 and FIG. 5, in embodiments, the power jet nebulizer 10 may further comprise a mask coupler 180 to accommodate an industry standard mask 12. The mask coupler 180 enables the industry standard mask 12 to attach to the outlet port 120, thereby enabling the vapor to translate from the power jet nebulizer 10 to the industry standard mask 12 for the user to inhale. The mask coupler 180 comprises a tubular body 181 with a first end 182, a second end 183 opposite the first end 182, and an aperture 184. The aperture 184 extends entirely through the tubular body 181, from the first end 182 to the second end 183. The first end 182 of the mask coupler 180 attaches to the industry standard mask 12. The second end 183 of the mask coupler 180 attaches to the outlet port 120 via friction fit. In embodiments, the mask coupler 180 comprises a smaller diameter than the aperture 122 of the outlet port 120. This enables the mask coupler 180 to be secured to the outlet port 120. The aperture 184 of the mask coupler 180 is in fluid communication with the aperture 122 of the outlet port 120, thereby enabling medicated vapor to translate from the power jet nebulizer 10 to the industry standard mask 12.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a power jet nebulizer 10. The disclosure is illustrated by example in the drawing figures, and throughout the written description. It should be understood that numerous variations are possible, while adhering to the inventive concept. Such variations are contemplated as being a part of the present disclosure.

What is claimed is:

1. A nebulizer configured to mix air with liquid medication and form a medicated wet vapor, comprising:

a bottom bowl configured to receive liquid medication and provide an area for air to mix with the liquid medication and form medicated wet vapor, the bottom bowl including an annular lip, a reservoir, and a stem configured to translate air from an exterior of the nebulizer into the nebulizer;

an inverted funnel configured to direct the flow of air entering the nebulizer to the reservoir, the inverted funnel including a first end, a second end, and a cavity extending therethrough, a notched collar extending around the first end of the inverted funnel and a plurality of feet disposed on the second end of the inverted funnel, the notched collar configured to guide the flow of the liquid medication into the reservoir of the bottom bowl and guide the flow of the medicated wet vapor upwardly through the nebulizer;

a turbo cap configured to guide the liquid medication inserted into the nebulizer to the bottom bowl, the turbo cap including an upper end, a lower end, an internal cavity, a shoulder including an upper end and a lower end, a funnel protruding upwardly from the upper end of the turbo cap, the funnel including an aperture in fluid communication with the internal cavity of the turbo cap, a lip protruding downwardly from the lower end of the shoulder and including an opening in fluid communication with the internal cavity of the turbo cap, and a vent including an aperture in fluid communication with the internal cavity of the turbo cap; and a top bowl configured to receive and contain the medicated wet vapor, the top bowl including an upper end, a lower end, an inner surface, an outer surface, and an internal cavity, the lower end of the top bowl including a periphery edge defining an opening providing access to the internal cavity of the top bowl, an inlet port configured to receive the liquid medication therethrough, the inlet port disposed at the upper end of the top bowl and in fluid communication with the internal cavity of the top bowl, an outlet port configured to enable the medicated wet vapor to translate therethrough, the outlet port disposed at the upper end of the top bowl and in fluid communication with the internal cavity of the top bowl, wherein:

the bottom bowl is configured to house the inverted funnel, the turbo cap is configured to attach to the bottom bowl, and the top bowl is configured to attach to the bottom bowl to form an assembled configuration;

when the nebulizer is in the assembled configuration, the liquid medication inserted into the inlet port translates through the turbo cap into the reservoir of the bottom bowl; and the nebulizer is configured to mix air introduced into the reservoir of the bottom bowl with the liquid medication residing in the reservoir of the bottom bowl to form the medicated wet vapor and translate the medicated wet vapor to the top bowl.

2. The nebulizer of claim 1, wherein:

the bottom bowl further comprises a body including a base with an inner surface and an outer surface opposite the inner surface of the base, a bulging side wall with an inner surface, an outer surface opposite the inner surface of the bulging side wall, an upper end, a lower end opposite the upper end of the bulging side wall, and a periphery edge disposed at the upper end of the bulging side wall, the bulging side wall interconnecting the base and the annular lip;

the annular lip disposed on the upper end of the bulging side wall and extending upwardly from the periphery edge of the bulging side wall, the annular lip including a perimeter edge defining an opening providing access to the reservoir of the bottom bowl;

the reservoir of the bottom bowl defined by the inner surface of the bulging side wall and the inner surface of the base; and the stem including an upper end, a lower end opposite the upper end of the stem, and an aperture extending entirely through the stem from the upper end of the stem to the lower end of the stem, the stem extending entirely through the base, from the outer surface of the base to the inner surface of the base, protruding upwardly from the inner surface of the base toward a center of the reservoir.

3. The nebulizer of claim 2, wherein the stem is disposed concentrically with respect to the body, the bulging side wall, and the annular lip.

4. The nebulizer of claim 2, wherein:

the base of the bottom bowl further includes a recess, the recess extends inwardly into the outer surface of the base; and the lower end of the stem is disposed at a center of the recess.

5. The nebulizer of claim 2, wherein the annular lip includes a threaded inner surface and a threaded outer surface.

6. The nebulizer of claim 2, wherein the base of the bottom bowl is substantially planar such that the base may be disposed on a flat surface without falling over.

7. The nebulizer of claim 5, wherein the inverted funnel further comprises a conical body which tapers in width from the second end of the inverted funnel to the first end of the inverted funnel, such that the second end of the inverted funnel includes a greater width than the first end of the inverted funnel, and a raised nipple concentrically positioned at the first end of the inverted funnel, the nipple including an aperture which extends entirely through the nipple to the cavity of the inverted funnel, the cavity of the inverted cavity extends through the entire inverted funnel, from the first end of the inverted funnel to the second end of the inverted funnel.

8. The nebulizer of claim 7, wherein the cavity of the inverted funnel includes a greater height and width greater than the upper end of the stem.

9. The nebulizer of claim 7, wherein the notched collar includes at least one notch configured to guide the liquid medication into the reservoir of the bottom bowl and guide the flow of the medicated wet vapor upwardly through the nebulizer, the notch is recessed inwardly into the notched collar.

10. The nebulizer of claim 7, wherein:

the shoulder is circumferentially disposed around a tubular body, the tubular body includes an upper end and a lower end, the internal cavity of the turbo cap extends entirely through the tubular body, from the upper end of the tubular body to the lower end of the tubular body;

the funnel includes a first end and a second end opposite the first end of the funnel, the funnel tapers inwardly from the first end of the funnel to the second end of the funnel, such that the first end of the funnel includes a greater diameter than the second end of the funnel, the aperture of the funnel extends entirely through the funnel from the first end of the funnel to the second end of the funnel;

the lip of the turbo cap including a threaded outer surface, a first end, and a second end including a perimeter edge defining an opening extending entirely through the lip of the turbo cap from the second end of the lip of the turbo cap to the first end of the lip of the turbo cap; and the vent disposed within the lip of the turbo cap, adjacent to the first end of the lip of the turbo cap.

11. The nebulizer of claim 10, wherein the internal cavity of the top bowl is defined by the inner surface of the top bowl, the inner surface of the top bowl adjacent to the periphery edge of the top bowl is threaded.

12. The nebulizer of claim 11, wherein:

the inlet port protrudes upwardly from the outer surface of the top bowl, the outlet port protruding upwardly from the outer surface of the top bowl;

the inlet port includes an aperture extending entirely through the inlet port and the top bowl to the internal cavity of the top bowl providing access thereto; and the outlet port including an aperture extending entirely through the outlet port and the top bowl to the internal cavity of the top bowl creating fluid communication therebetween.

13. The nebulizer of claim 12, wherein:

the outlet port is horizontally offset from the inlet port;

the outlet port comprises a greater diameter than the inlet port; and the outlet port comprises a greater height than the inlet port.

14. The nebulizer of claim 10, wherein:

the cavity of the inverted funnel receives and encompasses the upper end of the stem, the threaded outer surface of the lip of the turbo cap engages the threaded inner surface of the annular lip of the bottom bowl, the threaded inner surface of the top bowl engages the threaded outer surface of the annular lip of the bottom bowl; and the plurality of feet of the inverted funnel contact the inner surface of the base of the bottom bowl, the lower end of the tubular body is disposed flush on the perimeter edge of the annular lip of the bottom bowl, the lower end of the top bowl is disposed flush on the periphery edge of the bulging side wall of the bottom bowl.

15. The nebulizer of claim 12, wherein:

the nebulizer includes a longitudinal axis which extends vertically along a center of the nebulizer; and the aperture of the stem, the aperture of the nipple, the aperture of the cap, the internal cavity of the tubular body of the turbo cap, the aperture of the funnel, and the aperture of the inlet port are vertically aligned along the longitudinal axis and are in fluid communication with each other.

16. The nebulizer of claim 2, wherein the lower end of the stem is configured to selectively attach to the tubing of an air tank, wherein air translates from the air tank through the tubing and into and through the aperture of the stem to the cavity of the inverted funnel.

17. The nebulizer of claim 2, wherein:

the periphery edge of the bulging side wall may further include a gasket configured to seal the bottom bowl and the top bowl when the top bowl is attached to the bottom bowl, thereby preventing air, medication, and vapor from exiting the nebulizer; and the lower end of the annular shoulder may further include a gasket configured to seal the turbo cap and the bottom bowl when the turbo cap is attached to the bottom bowl, thereby preventing air, medication, and vapor from exiting the nebulizer.

18. The nebulizer of claim 1, wherein the nebulizer is configured to accommodate pressure within the range of 8 psi-35 psi.

19. The nebulizer of claim 1, further comprising a mask, the mask comprising:

a body configured to cover a user's nose and mouth including a perimeter edge, an inner surface, an outer surface opposite the inner surface of the body, a reservoir, an upper end, and a lower end, the perimeter edge of the mask including a face seal configured to seal the mask against the user's face, the reservoir of the body configured to receive the medicated wet vapor from the top bowl;

a lip disposed on the lower end of the body including a first end adjacent to the body, a second end, and a side wall extending between the first end of the lip of the body and the second end of the lip of the body, the first end of the lip of the body adjacent to the body and the side wall of the lip of the body extends outwardly away from the outer surface of the body, an aperture extends entirely through the lip of the body from the first end of the lip of the body to the second end of the lip of the body and through the body providing access to the reservoir of the body;

a joint configured to interconnect the outlet port and the mask, the joint comprising a base, a cylindrical body, and an aperture, the base disposed within the aperture of the lip and including a first end and a second end, the cylindrical body including an upper end and a lower end opposite the upper end of the cylindrical body extending outwardly from the second end of the base, the aperture extending through the joint from the lower end of the cylindrical body to the first end of the base to provide access to the reservoir of the body.

20. The nebulizer of claim 19, wherein the lip of the body includes a retaining rim configured to seal where the lip of the body and the joint meet, thereby preventing the medicated wet vapor from escaping the mask.

21. The nebulizer of claim 19, wherein:

the cylindrical body comprises a smaller diameter than the aperture of the outlet port; and the cylindrical body selectively attaches to the outlet port via a friction fit.

22. The nebulizer of claim 19, wherein:

the base of the joint is substantially circular in shape;

the aperture of the lip of the body comprises substantially the same shape and size of the base; and the side wall of the lip of the body curves inwardly at the second end of the lip of the body.

23. The nebulizer of claim 1, further comprising a mask coupler configured to attach an industry standard mask to the nebulizer, the mask coupler comprising a tubular body including a first end, a second end, and an aperture extending through the tubular body from the first end of the tubular body of the mask coupler to the second end of the tubular body of the mask coupler, wherein:

the tubular body includes a diameter smaller than the aperture of the outlet port, the second end of the tubular body of the mask coupler attaches to the outlet port via friction fit;

the first end of the tubular body of the mask coupler attaches to the industry standard mask; and the aperture of the mask coupler is in fluid communication with the aperture of the outlet port, such that the medicated wet vapor may translate from the outlet port into the mask coupler, then into the industry standard mask.

* * * * *